United States Patent [19]
Cannon

[11] Patent Number: 5,248,257
[45] Date of Patent: * Sep. 28, 1993

[54] ORTHODONTIC BRACKET SYSTEM

[76] Inventor: James L. Cannon, 1225 Sherwood Park Dr., Gainesville, Ga. 30501

[*] Notice: The portion of the term of this patent subsequent to Jun. 23, 2009 has been disclaimed.

[21] Appl. No.: 872,446

[22] Filed: Apr. 23, 1992

Related U.S. Application Data

[63] Continuation-in-part of Ser. No. 626,760, Dec. 13, 1990, Pat. No. 5,123,838.

[51] Int. Cl.⁵ .............................................. A61C 3/00
[52] U.S. Cl. ........................................ 433/14; 433/24
[58] Field of Search ..................... 433/8, 9, 10, 14, 16, 433/17, 24

[56] References Cited

U.S. PATENT DOCUMENTS

| | | |
|---|---|---|
| 3,163,933 | 1/1965 | Begg et al. |
| 3,178,821 | 4/1965 | Kesling. |
| 3,178,822 | 4/1965 | Fogel et al. |
| 3,477,128 | 11/1969 | Andrews ........................... 433/24 X |
| 3,660,900 | 5/1972 | Andrews ........................... 433/24 X |
| 4,180,912 | 1/1980 | Kesling ............................. 433/8 X |
| 4,310,306 | 1/1982 | Wallshein ........................... 433/14 |
| 4,427,381 | 1/1984 | Hall ................................. 433/14 |
| 4,531,911 | 7/1985 | Creekmore .......................... 433/8 |
| 4,664,626 | 5/1987 | Kesling ............................. 433/8 X |
| 4,838,787 | 6/1989 | Lerner .............................. 433/14 |
| 4,877,398 | 10/1989 | Kesling ............................. 433/8 |
| 5,044,945 | 9/1991 | Peterson ............................ 433/8 |

OTHER PUBLICATIONS

Techniques and treatment, pp. 720-723, 725.
60852, Type 316L Stainless Steel Shot Form.
60854, Type 316L Stainless Steel Shot Form.
60856, Type 316L Stainless Steel Shot Form.
60860, Type 316L Stainless Steel Shot Form.
ES12001, Styrene-low density, GP Grade.
ES12003, Styrene-low density, GP Grade.

*Primary Examiner*—Gene Mancene
*Assistant Examiner*—Nicholas D. Lucchesi
*Attorney, Agent, or Firm*—Jones & Askew

[57] ABSTRACT

There is disclosed a set of orthodontic brackets for attachment to teeth of either the mandibular arch or the maxillary arch. The orthodontic brackets comprise a plurality body members each having a base surface, a top surface and two opposing side surfaces. Slots are formed in the top surface and in at least one of the side surfaces. The slots are positioned in the body members such that the top slot of one bracket of the set of brackets is provided with substantially the same in/out compensation as another bracket of the set and the side slot of one bracket of the set of brackets is provided with substantially the same in/out compensation as another bracket of the set.

6 Claims, 9 Drawing Sheets

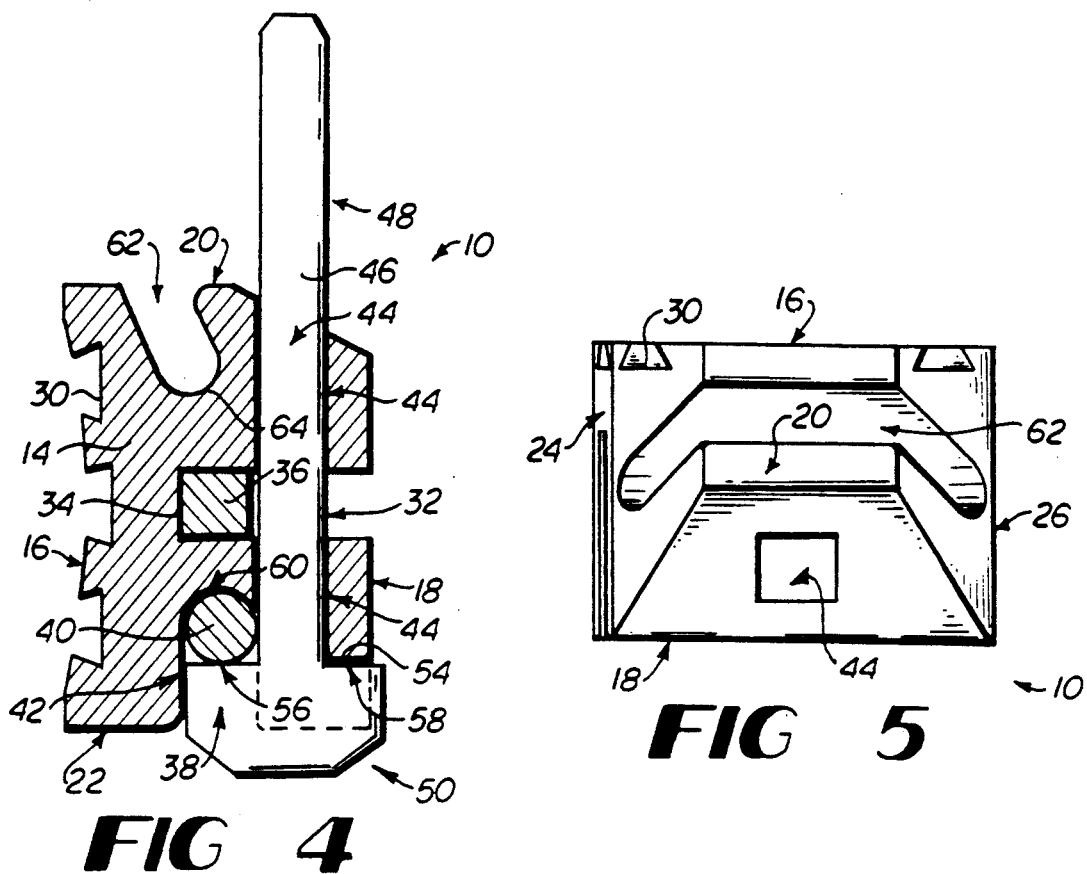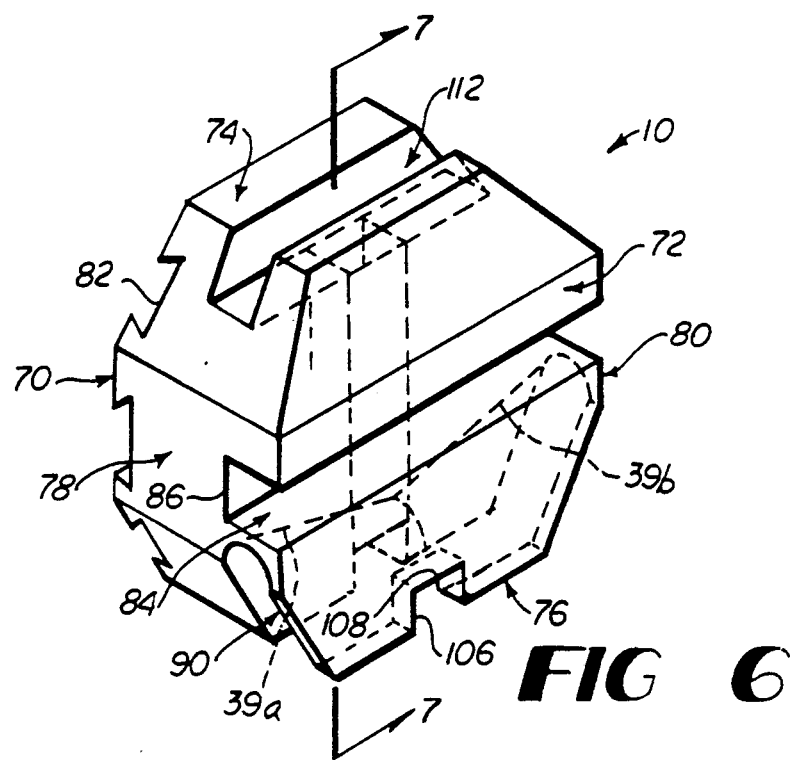

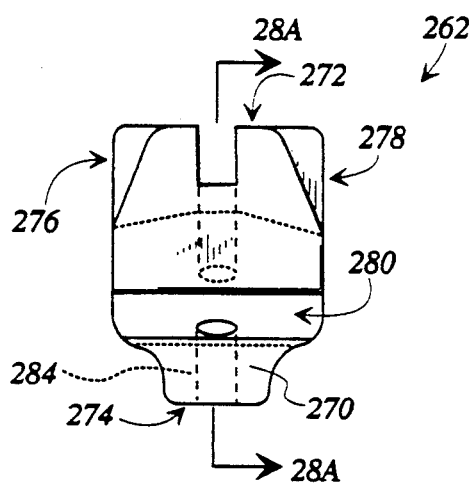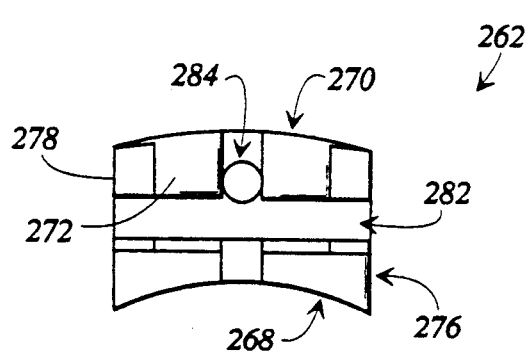
FIG 26
FIG 27

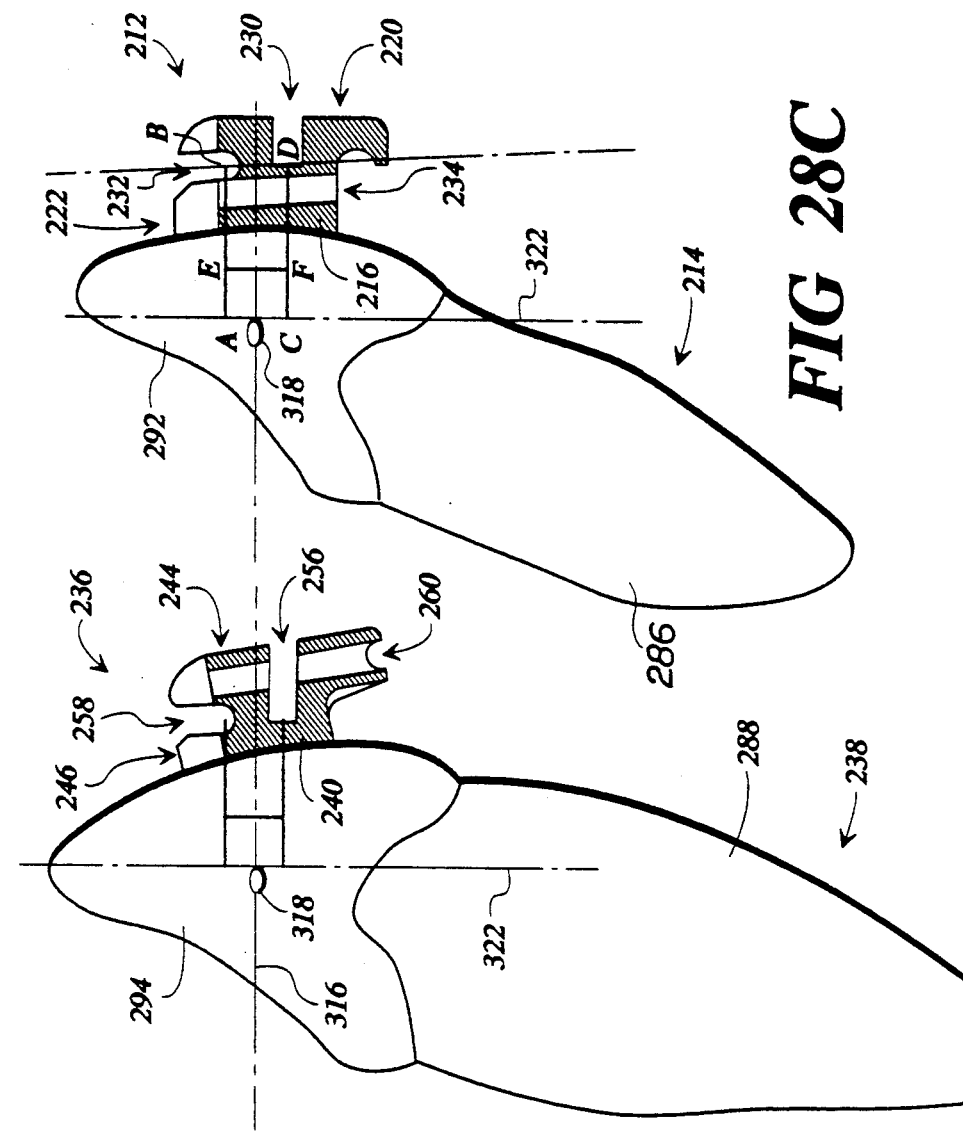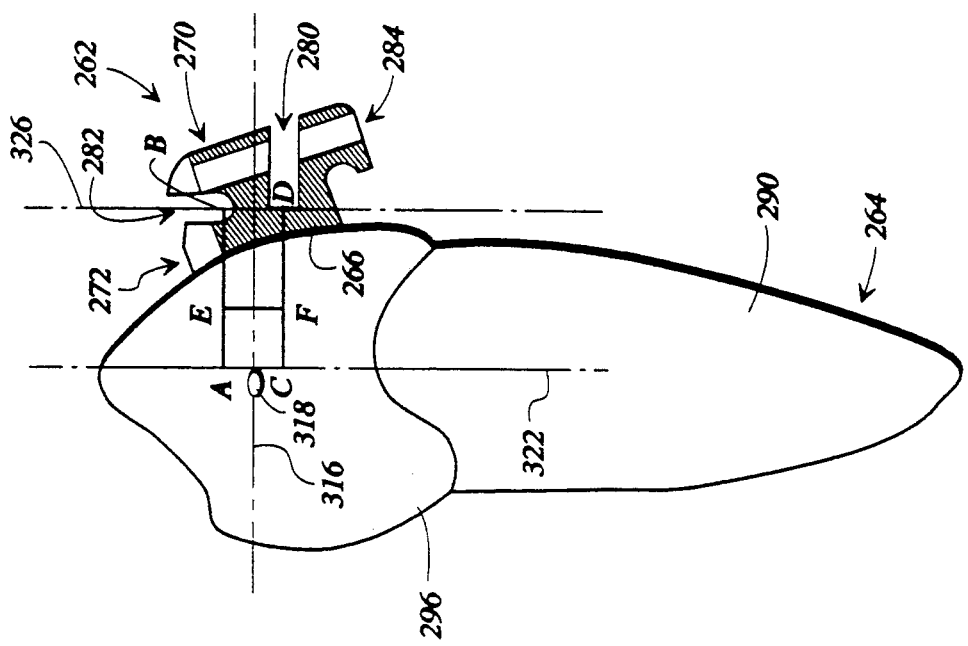

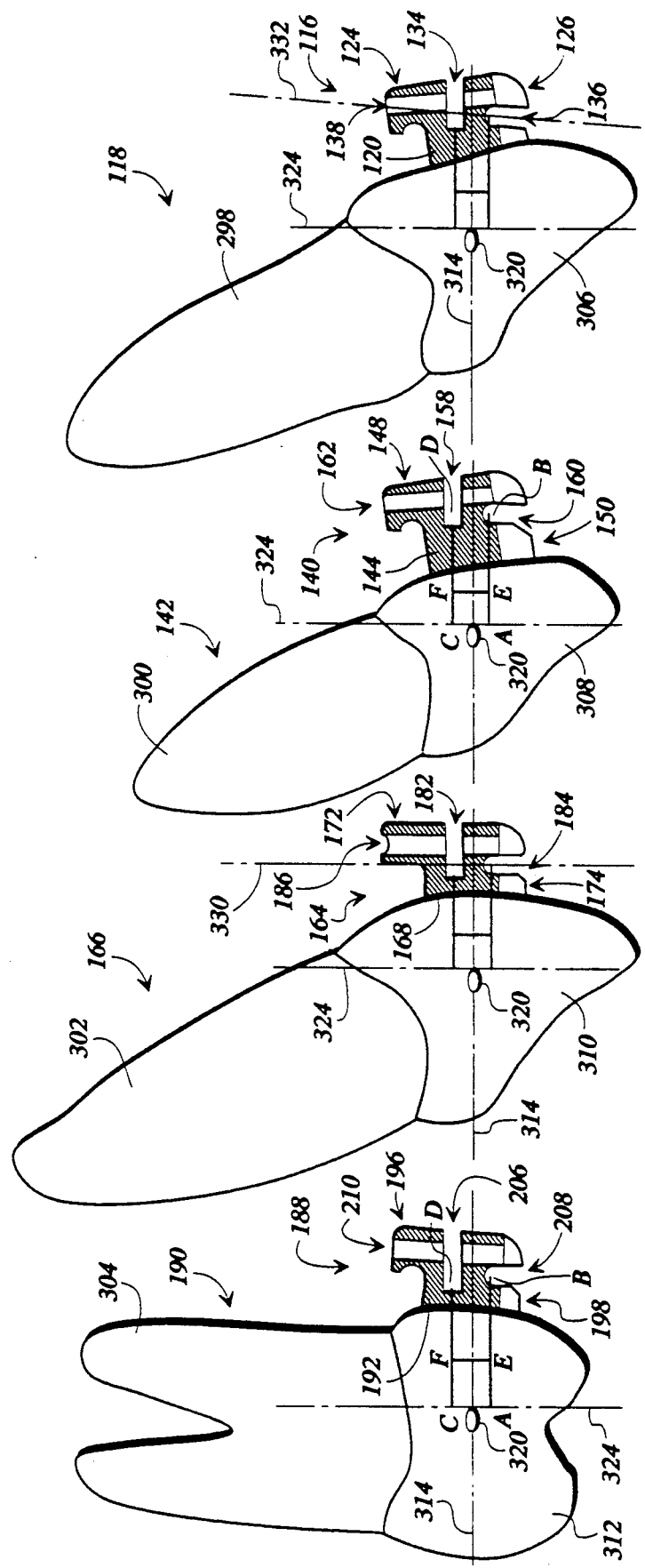

ORTHODONTIC BRACKET SYSTEM

CROSS-REFERENCE TO RELATED APPLICATIONS

This application is a continuation-in-part of application Ser. No. 626,760 filed Dec. 13, 1990, now U.S. Pat. No. 5,123,838.

FIELD OF INVENTION

The present invention relates generally to orthodontic brackets, and, more specifically, to a set of combination orthodontic brackets for use in the application of both the edgewise technique and the lightwire technique which brackets provides proper "in/out" compensation for both an edgewise slot and a lightwire slot. The present invention also includes an improved system for attaching and retaining both an archwire in the edgewise slot and archwire in the lightwire slot to an orthodontic bracket.

BACKGROUND OF THE INVENTION

Orthodontic brackets which are applied to teeth, either by attachment to a band or by direct bonding to a tooth, for the purpose of applying a moving force to the tooth to which the bracket is attached are known in the art. The moving force is generated by a wire attached to the orthodontic bracket which wire is also attached to similar brackets attached to adjoining teeth. The moving force applied to teeth over a period of time permits the movement of the teeth to accomplish desired alignment of the teeth.

There are two basic techniques for applying this moving force currently in practice in the orthodontic field. The conventional edgewise technique of applying this moving force is characterized by the use of a bracket having a rectangularly sectioned archwire receiving slot (edgewise slot). The moving force in this type of bracket (edgewise bracket) is applied to the tooth by the application of an angular or round sectioned archwire. The archwire is captured in the edgewise slot by a relatively small gauge stainless steel tie wire or by a small donut-shaped retaining member made from a resilient rubber-like material. The edgewise bracket is typically used for bodily movement of teeth. As a result of its design, that is, the archwire slot opening to the facial side of the bracket, only slight mesiodistal tipping of the brackets can occur when an archwire is engaged in the archwire slot.

A built-in design feature of other prior art edgewise brackets is "in/out" compensation. In/out compensation relates to the distance between the archwire slot and the base of the bracket (base thickness). Base thickness is determined for each bracket according to the crown facial prominence of the tooth to which that particular bracket is to be attached. Crown facial prominence is determined by measuring the distance from an imaginary line at the level of the crown's midtransverse plane that would connect the most facial portions of the contact areas of a single crown, or of all crowns, in an arch when they are optimally positioned, to each crown's most prominent facial point. This imaginary line is known as the embrasure line. The prior art brackets are designed to be attached to the teeth so that the occlusal/gingival midpoint of the edgewise slot is aligned with the most prominent facial point of each crown. If the teeth in the mandibular and/or maxillary arch are properly aligned a line drawn along the midtransverse plane of the teeth will pass through each crown's most prominent facial point. This line is know as the Andrews plane. A vertical line drawn perpendicular to Andrews plane that intersects the embrasure line at the most facial point of the distal contact area of each tooth, will be referred to hereafter as the Cannon plane. If the distance from the archwire slot to the Cannon plane is equal for all teeth in a given arch, proper in/out compensation is established for all the brackets in that arch. See L. Andrews, "Straight Wire- The Concept and Appliance," L.A. Wells Co., 1989.

Average maxillary crown facial prominence ranges from approximately 2.9 mm for upper first molars to 1.65 mm for upper lateral incisors. In the mandible arch, crown facial prominence ranges from 2.5 mm for lower first molars to 1.2 mm for lower anteriors. In the maxillary arch the first molar is the tooth with the greatest crown facial prominence, and, therefore, would have the bracket with the smallest base thickness. Likewise, the maxillary lateral incisors have the smallest crown facial prominence, and therefore, would have the bracket with the largest base thickness. The sum of the base thickness of the bracket and the crown facial prominence of the tooth is equal to the distance from the base of the edgewise slot to the Cannon plane. This same principal would also be true in the mandibular arch.

When an archwire is applied to a series of edgewise brackets with proper "in/out" compensation, a smooth curve of the archwire will meet all of the edgewise brackets. Therefore, a series of complicated bends do not have to be made in the archwire in order to properly engage each edgewise slot. The bending of an archwire to fit the "in/out" of a particular patient's teeth requires a significant amount of time and effort. Therefore, edgewise brackets with built in "in/out" compensation are desirable. An example of an edgewise orthodontic bracket with built-in "in/out" compensation is shown in U.S. Pat. No. 3,660,900.

The other orthodontic technique which is presently used is known as the Begg lightwire technique. This technique involves the use of a relatively light, round sectioned archwire. A lightwire bracket typically includes a gingival opening mesio-distally extending slot for receiving the archwire. The archwire slot, with its sloping mesial and distal shoulders, is designed to allow free tipping of the brackets on the archwire. The archwire is captured and secured in the archwire slot by a pin having an elongate body portion and an enlarged head portion. The pin is inserted into a slot in the body of the lightwire bracket which thereby captures the archwire between the head of the pin and the body of the bracket. The pin is then secured to the lightwire bracket by bending the elongate portion of the pin over the body of the bracket. An example of a lightwire bracket is shown in U.S. Pat. No. 3,178,821.

The aforementioned design of the archwire slot of the lightwire bracket in conjunction with the pin method of attaching an archwire thereto permits free tipping of the brackets (either labio-lingually or mesio-distally) on the archwire. Since heretofore, lightwire brackets of the prior art have not been known to include proper "in/out" compensation, a series of complicated bends must be made in the archwire in order to engage the archwire into the lightwire slot and have the moving force generated by the archwire result in optimum alignment of the teeth.

Both the edgewise technique and the lightwire technique have advantages under different circumstances. Furthermore, both techniques may be used at different times on the same patient. Therefore, in addition to edgewise brackets and lightwire brackets, there have been developed combination brackets. Such combination brackets permit the use of either the edgewise technique or the lightwire technique using the same bracket. Examples of such combination brackets are shown in U.S. Pat. Nos. 3,178,822 and 3,163,933. Although in/out compensation is provided in prior art combination brackets for an edgewise slot, in/out compensation has not heretofore been provided for both the edgewise slot and the lightwire slot.

Furthermore, because of the configuration of prior art orthodontic brackets, both an archwire in the edgewise slot and an archwire in the lightwire slot could not be attached to the bracket using a simple singular fastening pin. The use of a compound and/or complex fastening member to attach both an archwire in the edgewise slot and an archwire in the lightwire slot is undesirable because of the additional cost. Also, prior art combination brackets have heretofore been undesirably large causing difficulties in application and patient discomfort. Therefore, a combination orthodontic bracket has long been sought which can be used for both edgewise and lightwire corrective techniques, which provides proper "in/out" compensation in both the edgewise slot and the lightwire slot, which requires only a simple singular fastening member to attach both an archwire in the edgewise slot and an archwire in the lightwire slot to the bracket and which is relatively small and comfortable to wear.

SUMMARY OF THE INVENTION

The present invention satisfies the above-described needs by providing an improved orthodontic bracket and an improved orthodontic bracket system. The improved orthodontic bracket system of the present invention is designed for use on either the maxillary arch or the mandibular arch. The system comprises a plurality of discrete orthodontic brackets for attachment to teeth in an arch substantially on the Andrews plane of the teeth. Each of the brackets includes a body member having a base surface adapted for attachment to a tooth, a facial surface and two opposing sides. A first archwire slot is formed in the body member extending transverse the body member intermediate the two sides. The first archwire slot defines a base of said first archwire slot. A second archwire slot is formed in one of the sides of the body member extending transverse the body member intermediate the facial surface and the base surface. The second archwire slot defines a base of the second archwire slot. The bases of the first archwire slots are positioned in the body members such that the distances from the Cannon plane of the teeth to which the brackets are attached to the bases of the first archwire slots are substantially equal for all of the brackets in the respective arch. Additionally, the bases of the second archwire slots are positioned in the body members such that the distances from the Cannon plane of the teeth to which the brackets are attached to the bases of the second archwire slots are substantially equal for all of the brackets in the respective arch.

In another embodiment of the present invention, the orthodontic bracket comprises a body member having a base surface adapted for attachment to a tooth, a facial surface and two opposing sides. A first archwire slot formed in the body member extends transverse the body member intermediate the two sides opening at the facial surface and extending from the facial surface toward the base surface to a first distance from the base surface. The first archwire slot is sized and shaped for use in the edgewise corrective technique. A second archwire slot is formed in one of the sides of the body member extends transverse the body member intermediate the facial surface and the base surface. The second archwire slot is located a second distance from the base surface. The second archwire slot is sized and shaped for use in the lightwire corrective technique and includes mesial and distal sloped shoulders to permit tipping of the tooth when an archwire is received in the second archwire slot. A pin slot extends from one side to the other side of the body member. The pin slot is located intermediate the facial surface and the base surface at a third distance from the base surface greater than the first and second distances and such that when a pin is inserted in the pin slot, the pin can capture both an archwire in the first archwire slot and an archwire in the second archwire slot thereby attaching both archwires to the body member.

In another embodiment of the present invention, the orthodontic bracket comprises a solid body member having a base surface adapted for attachment to a tooth, a facial surface and two opposing sides. A first archwire slot is formed in the body member extending transverse the body member intermediate the two sides opening at the facial surface and extending from the facial surface toward the base surface to a first distance from the base surface. A second archwire slot is formed in one side of the body member intermediate the facial surface and the base surface, the second archwire slot being located a first distance from the base surface. A pin slot is formed in the body member extending from one side to the other side of the body member transverse the first and second archwire slots. The pin slot is located intermediate the facial surface and the base surface at a second distance from the base surface greater than the first distance and such that when a pin having an elongate body and a head at one end thereof is inserted in the pin slot, the body of the pin captures an archwire in the first archwire slot and the head of the pin captures an archwire in the second archwire slot thereby positioning both archwires in the body member the first distance from the base surface of the body member.

In yet another embodiment of the present invention the orthodontic bracket comprises a solid body member having a base surface adapted for attachment to a tooth, a facial surface and two opposing sides. A first archwire slot is formed in the body member extending transverse the body member intermediate the two sides opening at the facial surface and extending from the facial surface toward the base surface to a first distance from the base surface. A second archwire slot is formed in one side of the body member extending toward the other side of the body member intermediate the facial surface and the base surface, the second archwire slot being located the first distance from the base surface. A pin slot is formed in the body member extending from one side to the other side of the body member transverse the first and second archwire slots. The pin slot is located intermediate the facial surface and the base surface at a second distance from the base surface lesser than the first distance and such that when a pin having an elongate body and a head at one end thereof is inserted in the pin slot, the head of the pin captures an archwire in the second archwire slot thereby positioning the archwire the first distance from the base surface of the body member.

Accordingly, it is an object of the present invention to provide an improved orthodontic bracket and an improved orthodontic bracket system.

Another object of the present invention is to provide an orthodontic bracket and a set of orthodontic brackets which provide proper "in/out" compensation for both an edgewise slot and a lightwire slot.

A further object of the present invention is to provide orthodontic brackets which are relatively small and comfortable to wear.

Still another object of the present invention is to provide an orthodontic bracket which can secure an archwire in the edgewise slot and an archwire in the lightwire slot using a simple singular fastening member.

Another object of the present invention is to provide an orthodontic bracket to which it is relatively easy to attach both an archwire in the edgewise slot and an archwire in the lightwire slot.

Yet another object of the present invention is to provide an orthodontic bracket which positions an archwire fastening member between the archwire slots and the base of the bracket.

Still another object of the present invention is to provide an orthodontic bracket which has a relatively low profile.

These and other objects, features and advantages of the present invention will become apparent after a review of the following detailed description of the disclosed embodiments and the appended drawing and claims.

BRIEF DESCRIPTION OF THE DRAWING

FIG. 4 is a cross-sectional view of the improved orthodontic bracket shown in FIG. 3 showing the attachment of both a square-shaped cross-section archwire and a lightwire with a pin.

FIG. 5 is an top plan view of the improved orthodontic bracket shown in FIG. 1.

FIG. 6 is a perspective view of an alternate embodiment of the improved orthodontic bracket of the present invention with the pin slot, lightwire slot and retaining slot shown in phantom.

FIG. 26 is a top plan view of an alternate disclosed embodiment of the improved orthodontic bracket of the present invention of use with lower bicuspid teeth.

FIG. 27 is a left side plan view of the improved orthodontic bracket shown in FIG. 26.

FIGS. 28A-28C is a diagrammatic mesial or distal view of a lower anterior, a lower cuspid and a lower bicuspid from a mandibular arch showing cross-sectional views of a set of the improved orthodontic brackets shown in FIGS. 22-24 attached thereto.

FIGS. 29A-29D is a diagrammatic mesial or distal view of an upper central, an upper lateral, and upper cuspid and an upper bicuspid from a maxillary arch showing cross-sectional views of a set of the improved orthodontic brackets shown in FIGS. 14-21 attached thereto.

DETAILED DESCRIPTION OF THE DISCLOSED EMBODIMENTS

Figure 1:
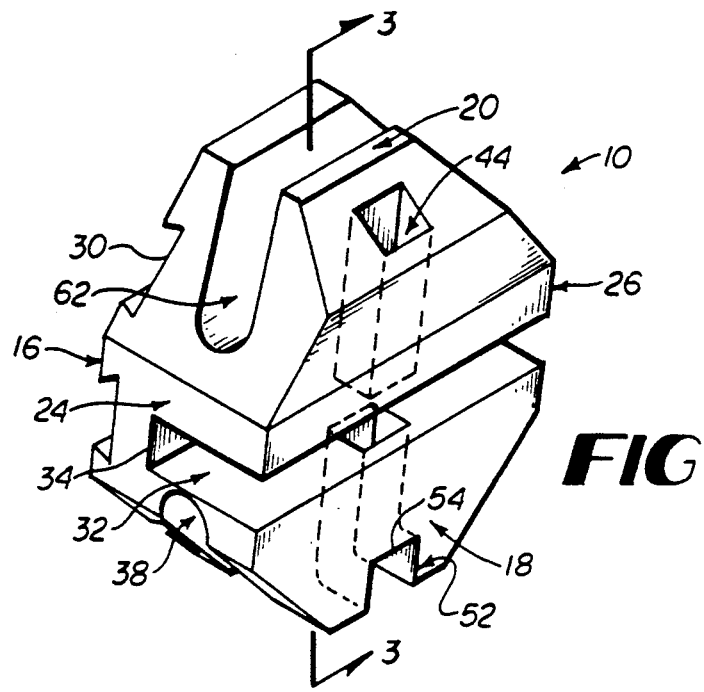
FIG. 1 is a perspective view of a disclosed embodiment of the improved orthodontic bracket of the present invention with a pin slot shown in phantom.
Figure 2:
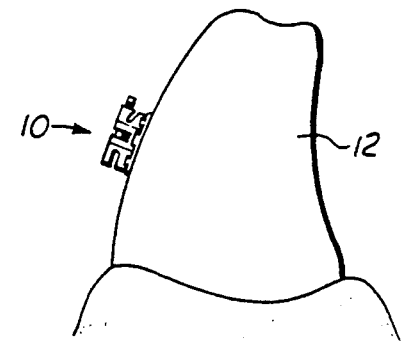
FIG. 2 is a side view of the improved orthodontic bracket shown in FIG. 1 attached to a tooth.

With reference to the drawing in which like numbers indicate like elements throughout the several views, it can be seen that there is an orthodontic bracket 10 for temporary attachment to a tooth 12 (FIG. 2) using well known conventional adhesive or cementing techniques. The particular method used to attach the bracket 10 to a tooth does not form a part of the present invention.

The bracket 10 is made from a solid piece of surgical stainless steel. The bracket 10, in the various configurations, as will be described below, can be made by machining a solid block of material, or, preferably, by casting using techniques well known in the art, such as the lost wax technique.

With reference to FIGS. 1 through 5, 10 and 11, there is shown a first embodiment of the present invention in which the bracket 10 comprises a body member 14 having a base surface 16, a facial surface 18, an occlusal surface 20, a gingival surface 22, a left surface 24 and a right surface 26. The base surface 16 includes a plurality of dovetail-shaped slots 30 formed therein. The base surface 16 is sized and shaped to be attached to the tooth 12. The dovetail-shaped slots 30 in the base surface 16 are provided so that the adhesive or cement which is used to attach the bracket 10 to the tooth 12 flows into the dovetail-shaped slots and more firmly anchors the bracket to the adhesive or cement.

The facial surface 18 of the body member 14 includes an edgewise slot 32 formed therein. The edgewise slot 32 has a rectangularly-shaped cross-section and extends from the facial surface 18 toward the base surface 16 and terminates a predetermined distance from the base surface. The bottom 34 of the edgewise slot 32 is therefore spaced from the base surface 16 a desired distance. The edgewise slot 32 is sized and shaped to receive an archwire 36 having an angular or round cross-section.

The gingival surface 22 has a lightwire slot 38 formed therein. The lightwire slot 38 extends from the gingival surface 22 toward the occlusal surface 20 and terminates a predetermined distance from the edgewise slot 32. The lightwire slot 38 is sized and shaped to receive a lightwire archwire 40 having a round-shaped cross-section. The lightwire slot 38 includes shoulders 39a, 39b which slope toward the occlusal surface 74 from a central point in the lightwire slot outwardly toward the left surface 24 and the right surface 26 (i.e., in the mesio and distal directions.) The sloping shoulders 39a, 39b permit the bracket 10 to freely tip about a lightwire archwire received in the lightwire slot 38.

The lightwire slot 38 includes a side wall 42 proximate the base surface 16. The lightwire slot 38 is positioned in the gingival surface 22 between the base surface 16 and the facial surface 18 so that the side wall 42 is located the same distance from the base surface 16 as the bottom 34 of the edgewise slot 32. When the archwire 36 and the archwire 40 are positioned in the edgewise slot 32 and the lightwire slot 38 respectively, both archwires are positioned the same distance from the base surface 16.

The body member 14 of the bracket 10 also includes a pin slot 44 which extends from the gingival surface 22 to the occlusal surface 20 intermediate the facial surface 18 and the lightwire slot 38 substantially parallel the facial surface and transverse the edgewise slot 32. The pin slot 44 is sized and shaped to receive a T-shaped retaining pin 46 having a elongate portion 48 and an enlarged head portion 50. The pin slot 44 is further positioned so that when the elongate portion 48 of the pin 46 is inserted in the pin slot 44, as shown in FIG. 4, the pin captures the archwire 36 between the pin and the body member 14 of the bracket 10 thereby retaining the archwire in the edgewise slot 32 adjacent the bottom 34 thereof.

The facial surface 18 has a notch 52 formed therein adjacent the gingival side surface 22. The notch 52 extends from the facial surface 18 to the lightwire slot 38. The notch 52 also extends from the gingival side surface 22 toward the occlusal surface 20 terminating at an end 54. The head portion 50 of the pin 46 includes shoulders 56, 58. When the pin 46 is inserted in the pin slot 44 such that the shoulder 58 of the head portion 50 of the pin abuts the end 54 of the notch 52, as shown in FIG. 4, the shoulder 56 of the head portion captures the archwire 40 in the lightwire slot 38 adjacent the end 60 thereof.

The occlusal side surface 20 optionally has a retaining slot 62 formed therein. The retaining slot 62 is located on the occlusal side surface 20 intermediate the base surface 16 and the pin slot 44. The retaining slot 62 extends from the occlusal side surface 20 toward the gingival side surface 22 at an angle toward the facial surface 18 and terminates at an end 64.

In order to use the bracket 10 of the present invention, the base surface 16 is adhered to the tooth 12 in the conventional manner using a well known adhesive or cement. With reference to FIG. 4, the archwire 36 is positioned in the edgewise slot 32 adjacent the bottom 34 thereof. The archwire 40 is then positioned in the lightwire slot 38 adjacent the end 60 thereof. The pin 46 is then inserted in the pin slot 44 so that the shoulder 58 abuts the end 54 of the notch 52. The free end of the elongate portion 48 of the pin 46 is then bent toward the right surface 26 so that the pin is retained in the pin slot.

As can be seen from the foregoing, when this particular bracket is used in this configuration, both the archwire 36 and the archwire 40 are positioned the same distance from the bottom surface 16 of the body 14, thereby providing the same "in/out" compensation for both wires. Furthermore, both the archwire 36 and the archwire 40 are retained in their respective slots 32, 38 by a simple singular retaining member, i.e., the pin 46.

Figure 3:
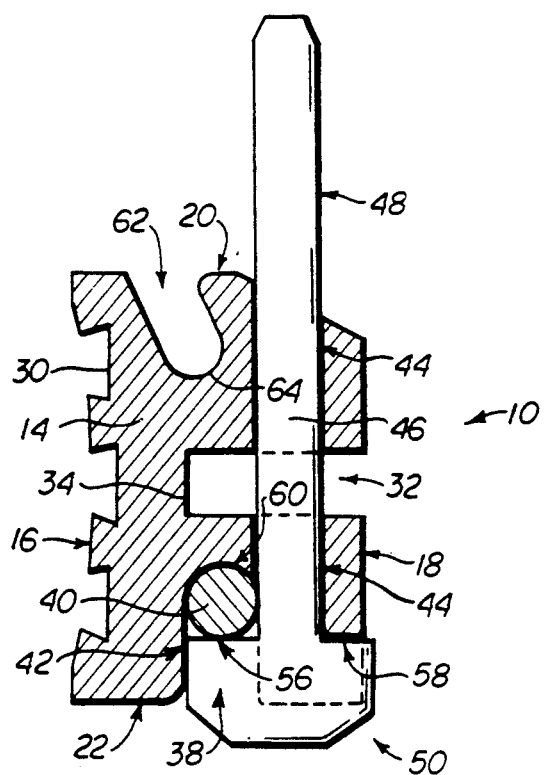
FIG. 3 is a cross-sectional view taken along the line 3—3 of the improved orthodontic bracket shown in FIG. 1 showing the attachment of a single lightwire archwire with a pin.

If it is desired to not use the pin 46 to hold both the archwire 36 and the archwire 40 in place a conventional tie wire (not shown), but well known in the art, can be used by looping the tie wire through the retaining slot 62, over the facial surface 18 and through the lightwire slot 38. The same retaining system, i.e., either the pin 46, or the tie wire, can be used to retain either a single archwire 36 in the edgewise slot 32 or a single archwire 40 in the lightwire slot 38, as shown in FIG. 3.

With reference to FIGS. 6 through 9, 12 and 13, there is shown a second embodiment of the present invention in which the bracket 10 comprises a body member 68 having a base surface 70, a facial surface 72, an occlusal surface 74, a gingival surface 76, a left surface 78 and a right surface 80. The base surface 70 includes a plurality of dovetail-shaped slots 82 formed therein. The base surface 70 is sized and shaped to be attached to the tooth 12. The dovetail-shaped slots 82 in the base surface 70 are provided so that the adhesive or cement which is used to attach the bracket 10 to the tooth 12 flows into the dovetail-shaped slots and more firmly anchors the bracket to the adhesive or cement.

The facial surface 72 of the body member 68 includes an edgewise slot 84 formed therein. The edgewise slot 84 has a rectangularly-shaped cross-section and extends from the facial surface 72 toward the base surface 70 and terminates a predetermined distance from the base surface. The bottom 86 of the edgewise slot 84 is therefore spaced from the base surface 70 a desired distance. The edgewise slot 84 is sized and shaped to receive an archwire 88 having an angular or round cross-section.

The gingival surface 76 has a lightwire slot 90 formed therein. The lightwire slot 90 extends from the gingival surface 76 toward the occlusal surface 74 and terminates a predetermined distance from the edgewise slot 84 at an end 92. The lightwire slot 90 is sized and shaped to receive an archwire 94 having a round-shaped cross-section.

The lightwire slot 90 includes a side wall 96 proximate the base surface 70. The lightwire slot 90 is positioned in the gingival surface 76 between the base surface 70 and the facial surface 72 so that the side wall 96 is located the same distance from the base surface 70 as the bottom 86 of the edgewise slot 84. When the archwire 88 and the archwire 94 are positioned in the edgewise slot 84 and the lightwire slot 90 respectively, the archwires are both positioned the same distance from the base surface 70. It is this distance of the archwire 88 and archwire 94 from the base surface 70 which represents for the archwire slots of this particular bracket the "in/out" compensation. Therefore, it can be seen that both the edgewise and lightwire slots of bracket 10 shown in FIGS. 3, 4, 7 and 8 are positioned in the body of the bracket the same distance from the base surface, i.e., both archwire slots have the same "in/out" compensation. This occurs in bracket 10 because a line drawn along the vertical (occlusal/gingival) plane of the base surface of bracket 10 is parallel to the Cannon plane, therefore, if both archwire slots are equal distance to the base surface and the base surface is parallel to the Cannon plane then both archwire slots are equal distance from the Cannon plane. This does not mean, however, that all brackets, where a vertical plane along the base surface is parallel to the Cannon plane would, necessarily have both archwire slots equal distance to either the base surface or the Cannon plane.

The body member 68 of the bracket 10 also includes a pin slot 98 which extends from the gingival surface 76 to the occlusal surface 74 intermediate the bottom 86 of the edgewise slot 84 and the side wall 96 of the lightwire slot 90 and the base surface 70 substantially parallel to the base surface and transverse the edgewise slot. The pin slot 98 is sized and shaped to receive an L-shaped retaining pin 100 having an elongate portion 102 and a leg portion 104. By positioning the pin slot 98 within the body member 68 in this manner, the labio/lingual profile, i.e., the distance from the base surface 70 to the facial surface 72, is reduced compared to other conventional brackets.

Figure 7:
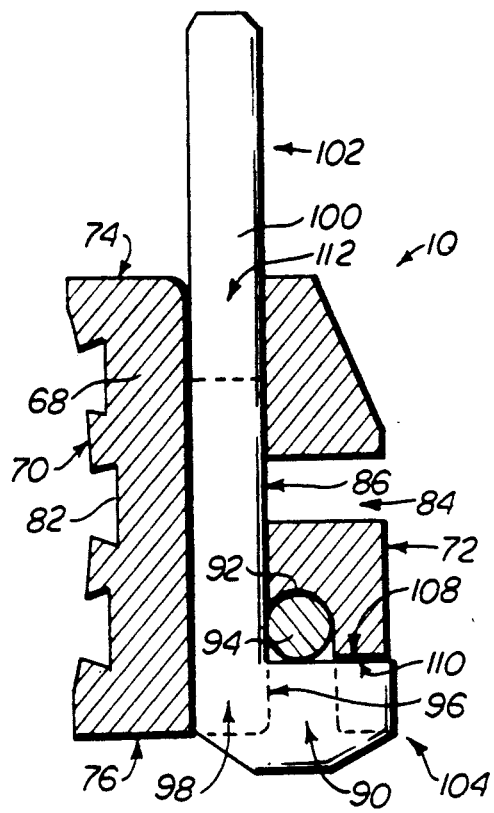
FIG. 7 is a cross-sectional view taken along the line 7—7 of the improved orthodontic bracket shown in FIG. 6 showing the attachment of a single lightwire archwire with a pin.

The facial surface 72 has a notch 106 formed therein adjacent the gingival side surface 76. The notch 106 extends from the facial surface 72 to the lightwire slot 90. The notch 106 also extends from the gingival side surface 76 toward the occlusal surface 74 terminating at an end 108. The leg portion 104 of the pin 100 includes a shoulder 110. When the pin 100 is inserted in the pin slot 98 such that the shoulder 110 of the leg portion 104 of the pin abuts the end 108 of the notch 106, as shown in FIG. 7, the shoulder of the leg portion captures the archwire 94 in the lightwire slot 90 adjacent the end 92 thereof.

The occlusal side surface 74 has a retaining slot 112 formed therein. The retaining slot 112 is located on the occlusal side surface 74 intermediate the base surface 70 and the facial surface 72 and coplanar with the pin slot 98. The retaining slot 112 extends from the left side surface 78 to the right side surface 80.

Figure 8:
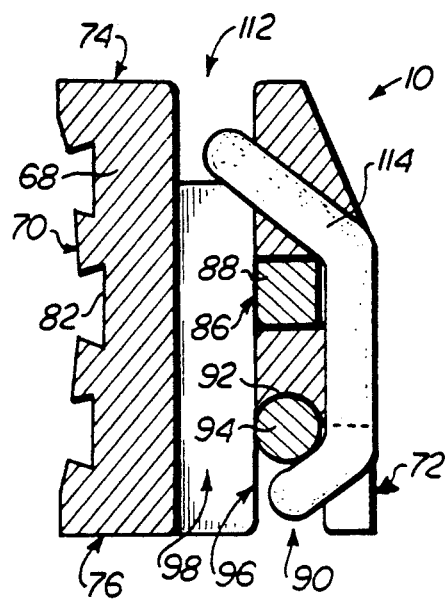
FIG. 8 is a cross-sectional view of the improved orthodontic bracket shown in FIG. 7 showing the attachment of both a square-shaped cross-section archwire and a lightwire archwire with a tie wire.
Figure 9:
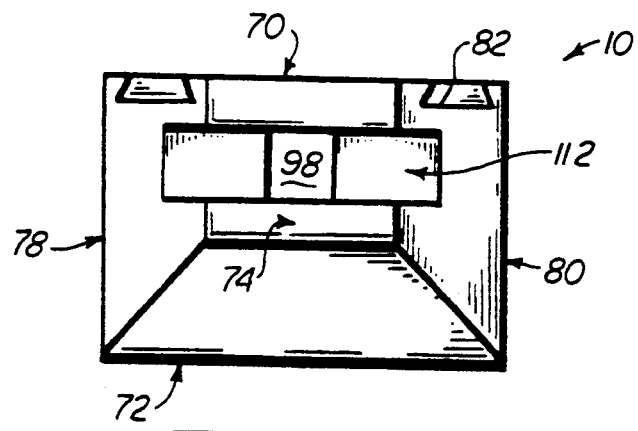
FIG. 9 is an top plan view of the improved orthodontic bracket shown in FIG. 6.
Figure 10:
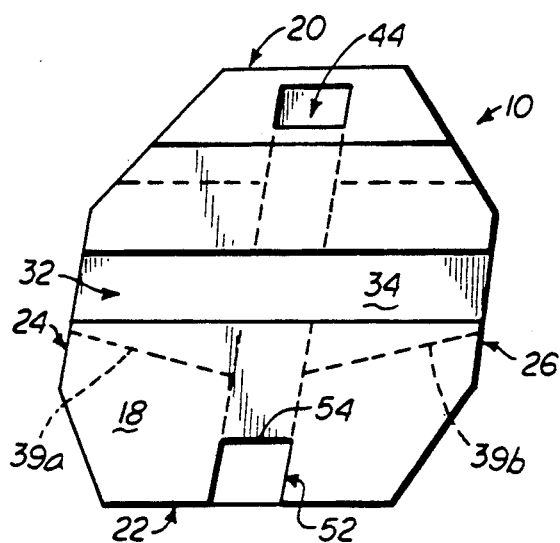
FIG. 10 is a right side plan view of the improved orthodontic bracket shown in FIG. 1 with the pin slot, lightwire slot and retaining slot shown in phantom.
Figure 11:
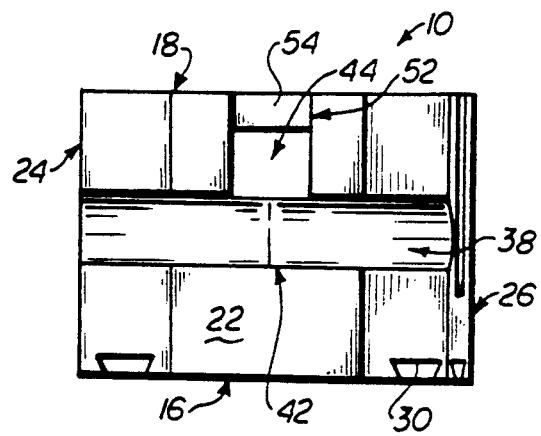
FIG. 11 is a bottom plan view of the improved orthodontic bracket shown in FIG. 6.
Figure 12:
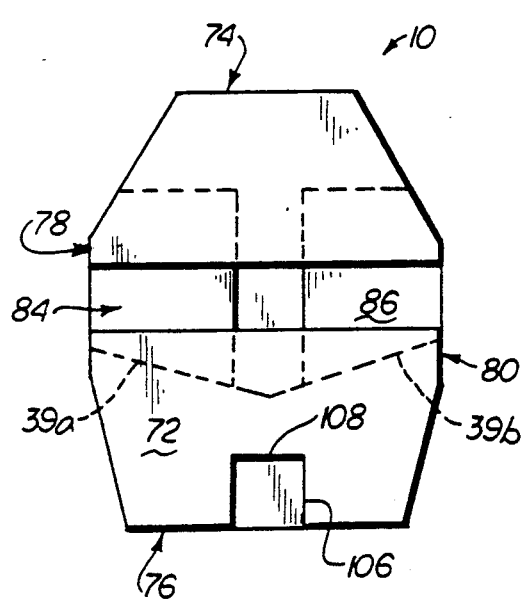
FIG. 12 is a right side plan view of the improved orthodontic bracket shown in FIG. 6 with the pin slot, lightwire slot and retaining slot shown in phantom.
Figure 13:
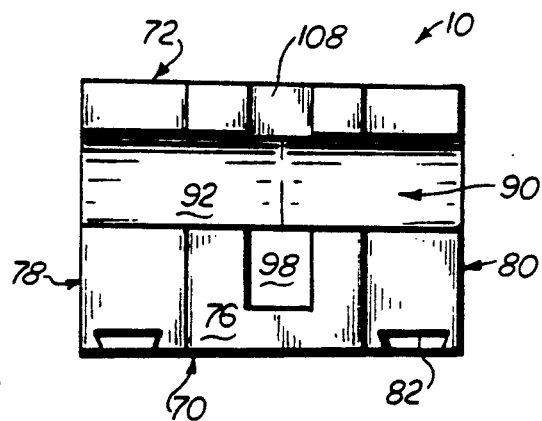
FIG. 13 is a bottom plan view of the improved orthodontic bracket shown in FIG. 6.

In order to use the bracket 10 of the present invention, the base surface 70 is adhered to the tooth 12 in the conventional manner using a well known adhesive or cement. With reference to FIG. 8, the archwire 88 is positioned in the edgewise slot 84 adjacent the bottom 86 thereof. The archwire 94 is then positioned in the lightwire slot 90 adjacent the end 92 thereof. A tie wire retaining member 114 is then inserted in the retaining slot 112 passed over the facial surface 72 and inserted into the lightwire slot 90, as shown in FIG. 8.

As can be seen from the foregoing, when the bracket of the present invention is used in this configuration, both the archwire 88 and the archwire 94 are positioned the same distance from both the base surface 70 of the body 68 and from the Cannon plane. Furthermore, both the archwire 88 and the archwire 94 are retained in their respective slots 84, 90 by a simple singular retaining member.

If it is desired to retain only a single archwire 94 in the lightwire slot 90, the same retaining system, i.e., the tie wire 114 can be used as described above. Alternately, as shown in FIG. 7, the pin 100 can also be used to retain the single archwire 94 in the lightwire slot 90. The archwire 94 is positioned in the lightwire slot 90 adjacent the end 92 thereof. The elongate portion 102 of the pin 100 is then inserted in the pin slot 112 so that the shoulder 110 of the leg portion 104 abuts the end 108 of the notch 106. The free end of the elongate portion 102 of the pin 100 is then bent toward either the left side 78 or the right side 80 to thereby secure the pin in the pin slot 98. As can be seen, the archwire 94 is captured in the lightwire slot 90 between the end 92 of the lightwire slot and the shoulder 110 of the pin 100 and retained thereby.

Further alternate embodiments of the present invention are shown in FIGS. 14–29. Only the principle elements of the brackets shown in FIGS. 14–29 will be described below. However, it should be understood that each of the brackets shown in FIGS. 14–29 include the same elements as described in detail hereinabove with respect to FIGS. 1–13.

Figure 14:
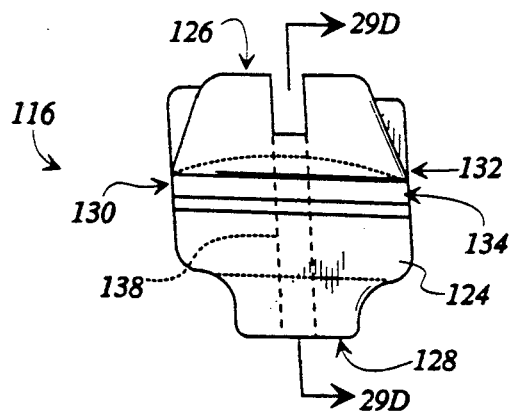
FIG. 14 is a top plan view of an alternate disclosed embodiment of the improved orthodontic bracket of the present invention of use with upper central teeth.
Figure 15:
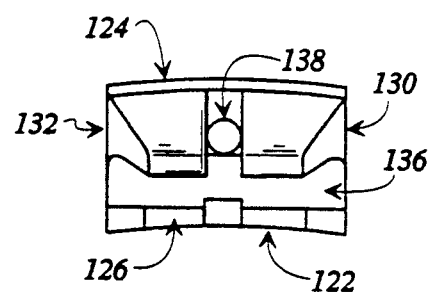
FIG. 15 is a left side plan view of the improved orthodontic bracket shown in FIG. 14.

FIGS. 14 and 15 show an orthodontic bracket 116 for temporary attachment to an upper central tooth 118 (FIG. 29d) of a maxillary arch. The bracket 116 comprises a body member 120 having a base surface 122, a facial surface 124, an occlusal surface 126, a gingival surface 128, a left surface 130 and a right surface 132. The facial surface 124 of the body member 120 includes an edgewise slot 134 formed therein. The occlusal surface 126 has a lightwire slot 136 formed therein. The body member 120 of the bracket 116 also includes a pin slot 138 which extends from the gingival surface 128 to the occlusal surface 126 intermediate the facial surface 124 and the lightwire slot 136 and transverse the edgewise slot 134.

Figure 16:
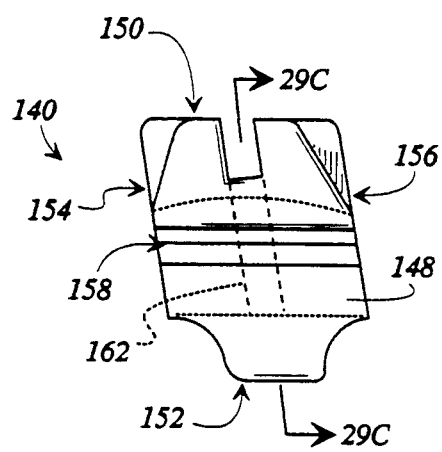
FIG. 16 is a top plan view of an alternate disclosed embodiment of the improved orthodontic bracket of the present invention of use with upper lateral teeth.
Figure 17:
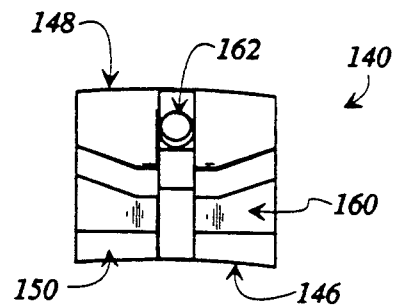
FIG. 17 is a left side plan view of the improved orthodontic bracket shown in FIG. 16.

FIGS. 16 and 17 show an orthodontic bracket 140 for temporary attachment to an upper lateral tooth 142 (FIG. 29c) of a maxillary arch. The bracket 140 comprises a body member 144 having a base surface 146, a facial surface 148, an occlusal surface 150, a gingival surface 152, a left surface 154 and a right surface 156. The facial surface 148 of the body member 144 includes an edgewise slot 158 formed therein. The occlusal surface 150 has a lightwire slot 160 formed therein. The body member 144 of the bracket 140 also includes a pin slot 162 which extends from the gingival surface 152 to the occlusal surface 150 intermediate the facial surface 148 and the lightwire slot 160 and transverse the edgewise slot 158.

Figure 18:
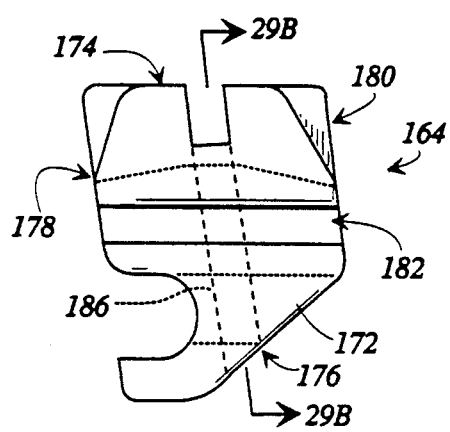
FIG. 18 is a top plan view of an alternate disclosed embodiment of the improved orthodontic bracket of the present invention of use with upper cuspid teeth.
Figure 19:
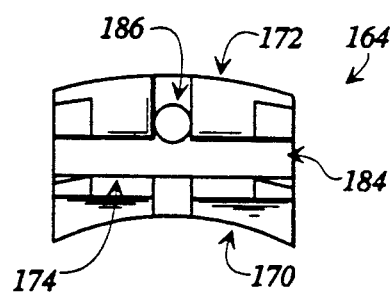
FIG. 19 is a left side plan view of the improved orthodontic bracket shown in FIG. 18.

FIGS. 18 and 19 show an orthodontic bracket 164 for temporary attachment to an upper canine or cuspid tooth 166 (FIG. 29b) of a maxillary arch. The bracket 164 comprises a body member 168 having a base surface 170, a facial surface 172, an occlusal surface 174, a gingival surface 176, a left surface 178 and a right surface 180. The facial surface 172 of the body member 164 includes an edgewise slot 182 formed therein. The occlusal surface 174 has a lightwire slot 184 formed therein. The body member 168 of the bracket 164 also includes a pin slot 186 which extends from the gingival surface 176 to the occlusal surface 174 intermediate the facial surface 172 and the lightwire slot 184 and transverse the edgewise slot 182.

Figure 20:
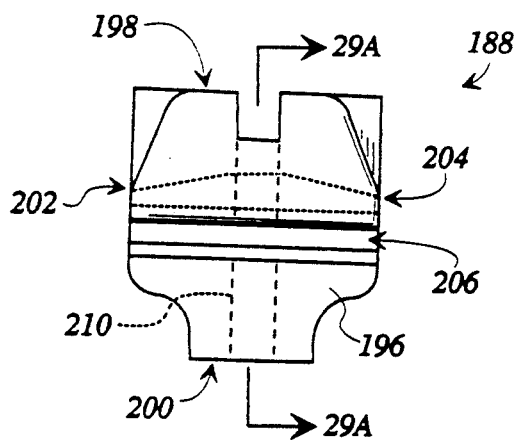
FIG. 20 is a top plan view of an alternate disclosed embodiment of the improved orthodontic bracket of the present invention of use with upper bicuspid teeth.
Figure 21:
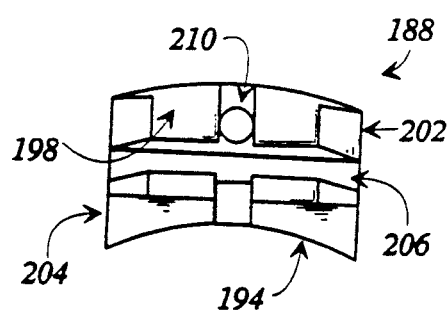
FIG. 21 is a left side plan view of the improved orthodontic bracket shown in FIG. 20.

FIGS. 20 and 21 show an orthodontic bracket 188 for temporary attachment to an upper bicuspid tooth 190 (FIG. 29a) of a maxillary arch. The bracket 188 comprises a body member 192 having a base surface 194, a facial surface 196, an occlusal surface 198, a gingival surface 200, a left surface 202 and a right surface 204. The facial surface 196 of the body member 192 includes an edgewise slot 206 formed therein. The occlusal surface 198 has a lightwire slot 208 formed therein. The body member 192 of the bracket 188 also includes a pin slot 210 which extends from the gingival surface 200 to the occlusal surface 198 intermediate the facial surface 196 and the lightwire slot 208 and transverse the edgewise slot 206.

Figure 22:
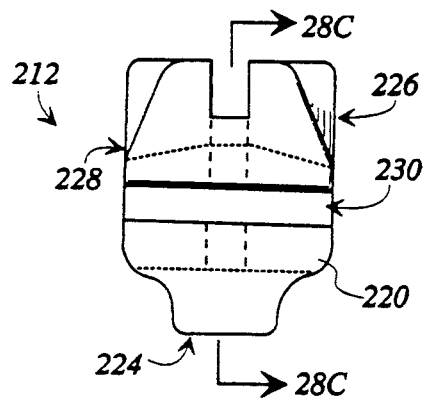
FIG. 22 is a top plan view of an alternate disclosed embodiment of the improved orthodontic bracket of the present invention of use with lower anterior teeth.
Figure 23:
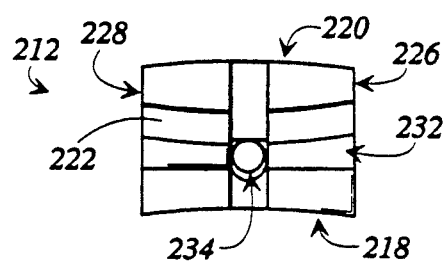
FIG. 23 is a left side plan view of the improved orthodontic bracket shown in FIG. 22.

FIGS. 22 and 23 show an orthodontic bracket 212 for temporary attachment to a lower anterior tooth 214 (FIG. 28c) of a mandibular arch. The bracket 212 comprises a body member 216 having a base surface 218, a facial surface 220, an occlusal surface 222, a gingival surface 224, a left surface 226 and a right surface 228. The facial surface 220 of the body member 216 includes an edgewise slot 230 formed therein. The occlusal surface 222 has a lightwire slot 232 formed therein. The body member 216 of the bracket 212 also includes a pin slot 234 which extends from the gingival surface 224 to the occlusal surface 222 intermediate the base surface 218 and the lightwire slot 232.

Figure 24:
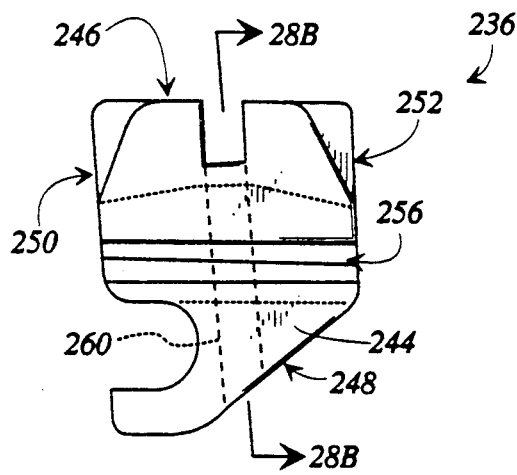
FIG. 24 is a top plan view of an alternate disclosed embodiment of the improved orthodontic bracket of the present invention of use with lower cuspid teeth.
Figure 25:
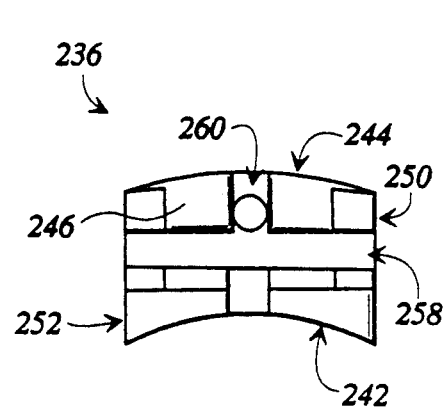
FIG. 25 is a left side plan view of the improved orthodontic bracket shown in FIG. 24.

FIGS. 24 and 25 show an orthodontic bracket 236 for temporary attachment to a lower canine or cuspid tooth 238 (FIG. 28b) of a mandibular arch. The bracket 236 comprises a body member 240 having a base surface 242, a facial surface 244, an occlusal surface 246, a gingival surface 248, a left surface 250 and a right surface 252. The facial surface 244 of the body member 240 includes an edgewise slot 256 formed therein. The occlusal surface 246 has a lightwire slot 258 formed therein. The body member 240 of the bracket 236 also includes a pin slot 260 which extends from the gingival surface 248 to the occlusal surface 246 intermediate the facial surface 244 and the lightwire slot 258 and transverse the edgewise slot 256.

FIGS. 26 and 27 show an orthodontic bracket 262 for temporary attachment to a lower bicuspid tooth 264 (FIG. 28a) of a mandibular arch. The bracket 262 comprises a body member 266 having a base surface 268, a facial surface 270, an occlusal surface 272, a gingival surface 274, a left surface 276 and a right surface 278. The facial surface 270 of the body member 266 includes an edgewise slot 280 formed therein. The occlusal surface 272 has a lightwire slot 282 formed therein. The body member 266 of the bracket 262 also includes a pin slot 284 which extends from the gingival surface 274 to the occlusal surface 272 intermediate the facial surface 270 and the lightwire slot 282 and transverse the edgewise slot 280.

With reference to FIGS. 28A-28C, there are shown three teeth 214, 238 and 264 which are representative of the teeth in a mandibular arch. Each of these teeth 214, 238 and 264 includes a root portion 286, 288 and 290 and a crown portion 292, 294 and 296, respectively. With reference to FIGS. 29A-29D, there are shown four teeth 118, 142, 166 and 190 which are representative of the teeth in a maxillary arch. Each of these teeth 118, 142, 166 and 190 includes a root portion 298, 300, 302 and 304 and a crown portion 306, 308, 310 and 312.

All of the teeth shown in FIGS. 28A-28C and 29A-29D are shown in their relative optimal position, i.e., the position for achieving a proper bite. Passing horizontally through the teeth 118, 142, 166 and 190 and through the teeth 212, 238 and 264 are imaginary lines 314 (FIGS. 29A-29D) and 316 (FIGS. 28A-28C), respectively. The lines 314 and 316 represent the Andrews plane.

Laying in the Andrews plane 314, 316 at the approximate midpoint of the crown of each tooth is the distal contact area. The distal contact area is the area of a tooth which is in contact with the adjacent teeth when the teeth are optimally positioned. In FIGS. 28A-28C and 29A-29D, the distal contact areas are shown by the elliptical lines 318 and 320, respectively.

Perpendicular to the Andrews plane and intersecting the most facial point of the distal contact area of each tooth is the Cannon plane. In FIGS. 28A-28C and 29A-29D, the Cannon plane is shown by the vertical lines 322 and 324, respectively.

Mounted on the face of each crown 292, 294 and 296 of the teeth 214, 238 and 264 is a bracket 212, 236 and 262, respectively. Similarly, mounted on the face of each crown 306, 308, 310 and 312 of the teeth 118, 142, 166 and 190 is a bracket 116, 140, 164 and 188. Preferably, each of these brackets is designed to be mounted to the crown of the tooth so that the occlusal/gingival midpoint of the brackets aligns on the Andrews plane and so that the Andrews plane passes between the edgewise slot and the base of the lightwire slot at the approximate midpoint. For example, as shown in FIG. 28, the Andrews plane 316 passes between the edgewise slot 256 and the lightwire slot 258 of the bracket 236 at the approximate midpoint. Similarly, as shown in FIG. 29, the Andrews plane 314 passes between the edgewise slot 182 and the lightwire slot 184 of the bracket 164 at the approximate midpoint.

Preferably, the edgewise slot is formed in the brackets of the present such that when the brackets are mounted on the crowns at the Andrews plane as described above, the longitudinal axis of the edgewise slot will be substantially parallel to the Andrews plane. For example, as shown in FIG. 28, the longitudinal axis of the edgewise slot 256 of the bracket 236 is substantially parallel to the Andrews plane 316. Similarly, as shown in FIGS. 29A-29D, the longitudinal axis of the edgewise slot 182 of the bracket 164 is substantially parallel to the Andrews plane 314.

The brackets of the present invention are designed to include a predetermined amount of in/out compensation. As described above, in/out compensation is necessary due to variation in crown facial prominence; that is, the distance from the embrasure line to each crown's most prominent facial point. "In/out" compensation is built into the brackets of the present invention by providing variable bracket base thickness. For example, the distance from the base surface 170 to the base of the edgewise slot 182 of the bracket 164 is relatively small because of the relatively great facial prominence of the crown 310 of the upper cuspid tooth 166 to which the bracket is attached. In contrast, the distance from the base surface 146 to the base of the edgewise slot 158 of the bracket 140 is relatively large because of the relatively small facial prominence of the crown 308 of the upper lateral tooth 142 to which the bracket is attached. Examples of various in/out compensation factors are disclosed in U.S. Pat. No. 3,660,900 (the disclosure of which is incorporated herein by reference).

When the brackets of the present invention are given proper in/out compensation, the distance from the base of the edgewise slot to the Cannon plane of the tooth to which the bracket is attached will be substantially equal for all the brackets in a given arch, i.e., either the maxillary arch or the mandibular arch. For example, the distance from the base of the edgewise slot 206 of the bracket 188 to the Cannon plane 324 of the tooth 190 (shown by the line C-D in FIG. 29a) is substantially equal to the distance from the base of the edgewise slot 158 to the Cannon plane 324 of the tooth 142 (shown by the line C-D in FIG. 29c). Similarly, the distance from the base of the edgewise slot 280 of the bracket 262 to the Cannon plane 322 of the tooth 264 (shown by the line C-D in FIG. 28a) is substantially equal to the distance from the base of the edgewise slot 230 to the Cannon plane 322 of the tooth 212 (shown by the line C-D in FIG. 28c).

However, it should be noted that the distance from the base of the edgewise slot to the Cannon plane of a tooth in the mandibular arch may not be substantially equal to the distance from the base of the edgewise slot to the Cannon plane of a tooth in the maxillary arch. For example, the distance from the base of the edgewise slot 280 of the bracket 262 to the Cannon plane 322 of the tooth 264 (shown by the line C-D in FIG. 28a) may not be substantially equal to the distance from the base of the edgewise slot 206 of the bracket 188 to the Cannon plane 324 of the tooth 190 (shown by the line C-D in FIG. 29a).

It is an essential feature of the present invention that the lightwire slot is formed in the body member of the bracket such that the base of the lightwire slot is positioned substantially the same distance from the Cannon plane for all brackets of a given arch when the brackets are mounted on the Andrews plane of the crowns of the teeth as described above. As used herein the base of the lightwire slot shall mean that portion of the lightwire slot occupied by the center of a wire captured in the lightwire slot by a retaining member, such as by a pin engaged in the pin slot, by a ligature tie or by other similar retaining means. For example, as shown in FIG. 28A-28C, the distance from the base of the lightwire slot 282 of the bracket 262 to the Cannon plane 322 of the tooth 264 (shown by the line A-B in FIG. 28a) is substantially equal to the distance from the base of the lightwire slot 232 of the bracket 212 to the Cannon plane 322 of the tooth 214 (as shown by the line A-B in FIG. 28c). Similarly, the distance from the base of the lightwire slot 208 of the bracket 188 to the Cannon plane 324 of the tooth 190 (shown by the line A-B in FIG. 29a) is substantially equal to the distance from the base of the lightwire slot 160 of the bracket 140 to the Cannon plane 324 of the tooth 142 (as shown by the line A-B in FIG. 29c).

However, it should be noted that the distance from the base of the lightwire slot to the Cannon plane of a tooth in the mandibular arch may not be substantially equal to the distance from the base of the lightwire slot to the Cannon plane of a tooth in the maxillary arch. For example, the distance from the base of the lightwire slot 282 of the bracket 262 to the Cannon plane 322 of the tooth 264 (shown by the line A-B in FIG. 28a) may not be substantially equal to the distance from the base of the lightwire slot 208 of the bracket 188 to the Cannon plane 324 of the tooth 190 (shown by the line A-B in FIG. 29a).

Preferably, the distance from the base of the edgewise slot to the base of the lightwire slot of the brackets of the present invention is substantially equal for all brackets in a given arch. For example, the distance from the base of the edgewise slot 280 to the base of the lightwire slot 282 of the bracket 262 (shown by the line E-F in FIG. 28a) is substantially equal to the distance from the base of the edgewise slot 230 to the base of the lightwire slot 232 of the bracket 212 (shown by the line E-F in FIG. 28c). Similarly, the distance from the base of the edgewise slot 206 to the base of the lightwire slot 208 of the bracket 188 (shown by the line E-F in FIG. 29a) is substantially equal to the distance from the base of the edgewise slot 158 to the base of the lightwire slot 160 of the bracket 140 (shown by the line E-F in FIG. 29c).

However, it should be noted that the distance from the base of the lightwire slot to the base of the edgewise slot of a bracket mounted to a tooth in the mandibular arch may not be substantially equal to the distance from the base of the lightwire slot to the base of the edgewise slot of a bracket mounted to a tooth in the maxillary arch. For example, the distance from the base of the edgewise slot 206 to the base of the lightwire slot 208 of the bracket 188 (shown by the line E-F in FIG. 29a) may not be substantially equal to the distance from the base of the edgewise slot 280 to the base of the lightwire slot 282 of the bracket 262 (shown by the line E-F in FIG. 28a).

The lightwire slots of the brackets of the present invention each have an axis which extends in an occlusal/gingival direction. When the brackets are attached to teeth in accordance with the present invention the axes of the lightwire slots are generally vertical. The lightwire slots are formed in the brackets of the present invention such that when the brackets are mounted on teeth in accordance with the present invention the axis of the lightwire slot of at least one bracket is substantially parallel to the Cannon plane of the tooth to which the bracket is attached and the axis the lightwire slot of at least another bracket intersects the Cannon plane of the tooth to which the bracket is attached on the occlusal side of that bracket.

With reference to the brackets shown in FIG. 28A-28C, it can be seen that the lightwire slot 282 of the bracket 262 has an axis 326 which extends in an occlusal/gingival direction. When the bracket 262 is mounted on the tooth 264, as shown in FIG. 28A, the axis 326 of the lightwire slot 282 is substantially parallel to the Cannon plane 322. In other words, the lightwire slot 282 is formed in the bracket 262 such that the occlusal/gingival axis of the lightwire slot is substantially parallel to the Cannon plane. Similarly, the lightwire slot 232 of the bracket 212 has an axis 328 which extends in the occlusal/gingival direction. However, when the bracket 212 is mounted on the tooth 214, as shown in FIG. 28C, the axis 328 of the lightwire slot 232 intersects the Cannon plane 322 on the occlusal side of the bracket. In other words, the lightwire slot 232 is formed in the bracket 212 such that the occlusal/gingival axis of the lightwire slot is at an acute angle with respect to the Cannon plane. Although the axis of the lightwire slot 258 is not shown, that axis is substantially parallel to the Cannon plane 322 of the tooth 238.

With reference to the brackets shown in FIG. 29A-29D, it can be seen that the lightwire slot 184 of the bracket 164 has an axis 330 which extends in an occlusal/gingival direction. When the bracket 164 is mounted on the tooth 166, as shown in FIG. 29B, the axis 330 of the lightwire slot 184 is substantially parallel to the Cannon plane 324. In other words, the lightwire slot 184 is formed in the bracket 164 such that the occlusal/gingival axis of the lightwire slot is substantially parallel to the Cannon plane. Similarly, the lightwire slot 136 of the bracket 116 has an axis 332 which extends in the occlusal/gingival direction. However, when the bracket 116 is mounted on the tooth 118, as shown in FIG. 29D, the axis 332 of the lightwire slot 136 intersects the Cannon plane 324 on the occlusal side of the bracket. In other words, the lightwire slot 136 is formed in the bracket 116 such that the occlusal/gingival axis of the lightwire slot is at an acute angle with respect to the Cannon plane. Although the axes of the lightwire slots 160, 208 are not shown, those axes are substantially parallel to the Cannon plane 324 of the teeth 142, 190.

The brackets of the present invention are used by installing the brackets on the appropriate teeth of a given arch, such as shown in FIGS. 28A-28C and 29A-29D, which teeth are in need of alignment to their optimal position. Archwires are installed in the edgewise slots and/or the lightwire slots. Initially, the archwires installed in the slots are of a relatively small gauge. Furthermore, since the teeth are not optimally aligned, the bases of the edgewise slots and the lightwire slots are not in the relative positions shown in FIGS. 28A-28C and 29A-29D. Accordingly, when unbent wires are installed in the edgewise slots and/or the lightwire slots, vector forces are applied to the brackets which will tend to move the teeth to which the brackets are attached toward the optimal positions, such as shown in FIGS. 28A-28C and 29A-29D. Successively larger gauge wires are installed in the edgewise and/or lightwire slots of the brackets as the teeth approach their optimal positions. When the teeth are optimally positioned, wires installed in the edgewise and/or lightwire slots will have a smooth, unbent curve which follows the embrasure line of the teeth. When such smooth curved wires are installed in the edgewise slots and/or lightwire slots of the brackets, the vector forces applied to the brackets by the archwires will be zero. Therefore, it can be seen that the vector forces applied to the brackets can be varied by using different gauge archwires and that as the teeth move toward their optimal positions, the vector forces applied to the brackets for a given gauge archwire will approach zero. This feature permits virtually automatic optimal positioning of the teeth with little risk of over correction and reduced labor due to the unbent shape of the archwires used the brackets.

It should be understood, of course, that the foregoing relates only to certain disclosed embodiments of the present invention and that numerous modifications or alterations may be made therein without departing from the spirit and scope of the invention as set forth in the appended claims.

What is claimed is:

1. An orthodontic bracket system for use on either the maxillary arch or the mandibular arch, said system comprising:
    a plurality of discrete orthodontic brackets for attachment to teeth in one of said arches;
    each of said brackets including a body member having a base surface adapted for attachment to a tooth, a facial surface and two opposing sides and also including,
    a first archwire slot formed in said body member extending transverse said body member intermediate one of said sides and the other of said sides, said first archwire slot defining a base thereof, said first archwire slot being sized and shaped for use in the edgewise corrective technique and,
    a second archwire slot formed in said one side of said body member extending toward said other side of said body member intermediate said facial surface and said base surface, said second archwire slot defining a base thereof, said second archwire slot being sized and shaped for use in the lightwire corrective technique, said second archwire slot including mesial and distal sloped shoulders to permit free tipping of said bracket when an archwire is received in said second archwire slot;
    said bases of said first archwire slots being positioned in said body members such that the distances from the Cannon plane of the teeth to which said brackets are to be attached to said bases of said first archwire slots are substantially equal for all said brackets;
    said bases of said second archwire slots being positioned in said body members such that the distances from the Cannon plane of the teeth to which said brackets are to be attached to said bases of said second archwire slots are substantially equal for all said brackets;
    a pin slot formed in said body member of at least one of said brackets intermediate said facial surface and said base of said first archwire slot and extending from said one side of said body member to said other side of said body member, said pin slot being for receiving a pin having an elongate body portion and an enlarged head, said pin slot being further located in said body member such that when said pin is received in said pin slot, a first archwire received in said first archwire slot is captured in said first archwire slot between said elongate body portion of said pin and said base of said first archwire slot and a second archwire received in said second archwire slot is captured in said second archwire slot between said base of said second archwire slot and said enlarged head of said pin, whereby both said first and second archwires are retained in said first and second archwire slots respectively by said pin; and
    a pin slot formed in said body member of at least one other of said brackets extending from said one side of said body member to said other side, said pin slot being for receiving an elongate pin for retaining an archwire in said second archwire slot, said pin slot not substantially intersecting either said first or said second archwire slots, said pin slot being located intermediate said base surface and said first and second archwire slots, such that the distance from said facial surface to said base surface of said body member is reduced thereby providing said bracket with a reduced labio/lingual profile.

2. The orthodontic bracket system of claim 1, wherein said second archwire slot of at least one of said brackets has an occlusal/gingival axis substantially parallel to the Cannon plane of the tooth to which said bracket is to be attached.

3. The orthodontic bracket system of claim 1, wherein said second archwire slot of at least one of said brackets has an occlusal/gingival axis which intersects the Cannon plane on the occlusal side of said bracket.

4. An orthodontic bracket comprising:
a body member having a base surface for attachment to a tooth, a facial surface and two opposing sides,
a first archwire slot formed in said body member extending transverse said body member intermediate one of said sides and the other of said sides, said first archwire slot being sized and shaped for use in the edgewise corrective technique, said first archwire slot including a base for receiving an archwire;
a second archwire slot formed in said one side of said body member extending toward said other side of said body member intermediate said facial surface and said base surface, said second archwire slot being sized and shaped for use in the lightwire corrective technique, said second archwire slot including mesial and distal sloped shoulders to permit free tipping of said bracket when an archwire is received in said second archwire slot; and
a pin slot formed in said body member intermediate said facial surface and said base of said first archwire slot and extending from said one side of said body member to said other side of said body member, said pin slot being for receiving a pin having an elongate body portion and an enlarged head, said pin slot being further located in said body member such that when said pin is received in said pin slot, a first archwire received in said first archwire slot is captured in said first archwire slot between said elongate body portion of said pin and said base of said first archwire slot and a second archwire received in said second archwire slot is captured in said second archwire slot by said enlarged head of said pin, whereby both said first and second archwires are retained in said first and second archwire slots respectively by said pin.

5. An orthodontic bracket comprising:
a body member having a base surface for attachment to a tooth, a facial surface and two opposing sides,
a first archwire slot formed in said body member extending transverse said body member intermediate one of said sides and the other of said sides, said first archwire slot being sized and shaped for use in the edgewise corrective technique;
a second archwire slot formed in said one side of said body member extending toward said other side of said body member intermediate said facial surface and said base surface, said second archwire slot being sized and shaped for use in the lightwire corrective technique, said second archwire slot including mesial and distal sloped shoulders to permit free tipping of said bracket when an archwire is received in said second archwire slot; and
a pin slot formed in said body member extending from said one side of said
a pin slot formed in said body member extending from said one side of said body member to said other side, said pin slot being for receiving an elongate pin for retaining an archwire in said second archwire slot, said pin slot being located intermediate said base surface and said first and second archwire slots, said pin slot not substantially intersecting either said first or said second archwire slots, such that the distance from said facial surface to said base surface is reduced thereby providing said body member with a reduced labio/lingual profile.

6. An orthodontic bracket system for use on either the maxillary arch or the mandibular arch, said system comprising:
a plurality of discrete orthodontic brackets for attachment to teeth in one of said arches;
each of said brackets including a body member having a base surface adapted for attachment to a tooth, a facial surface and two opposing sides and also including,
a first archwire slot formed in said body member extending transverse said body member intermediate one of said sides and the other of said sides, said first archwire slot defining a base thereof, said first archwire slot being sized and shaped for use in the edgewise corrective technique and,
a second archwire slot formed in said one side of said body member extending toward said other side of said body member intermediate said facial surface and said base surface, said second archwire slot defining a base thereof, said second archwire slot being sized and shaped for use in the lightwire corrective technique, said second archwire slot including mesial and distal sloped shoulders to permit free tipping of said bracket when an archwire is received in said second archwire slot;
said bases of said first archwire slots being positioned in said body members such that the distances from the Cannon plane of the teeth to which said brackets are to be attached to said bases of said first archwire slots are substantially equal for all said brackets;
said bases of said second archwire slots being positioned in said body members such that the distances from the Cannon plane of the teeth to which said brackets are to be attached to said bases of said second archwire slots are substantially equal for all said brackets;
a pin slot formed in said body member of at least one of said brackets extending from said one side of said body member to said other side, said pin slot being for receiving an elongate pin for retaining an archwire in said second archwire slot, said pin slot not substantially intersecting either said first or said second archwire slots, said pin slot being located intermediate said base surface and said first and second archwire slots, such that the distance from said facial surface to said base surface of said body member is reduced thereby providing said bracket with a reduced labio/lingual profile.

* * * * *